United States Patent

Reuss, Jr. et al.

[11] Patent Number: 5,827,174
[45] Date of Patent: Oct. 27, 1998

[54] BIOLOGICAL SPECIMAN CONTAINMENT AND INCUBATION POUCH

[76] Inventors: William Alexander Reuss, Jr., 4901 Lea Ann Way, Louisville, Ky. 40219; William Charles Mers Kelly, 1112 Glen Kegley Dr., Xenia, Ohio 45385; David Young Pheups, 904 Shady Ln., Anchorage, Ky. 40223

[21] Appl. No.: 877,523

[22] Filed: Jun. 17, 1997

Related U.S. Application Data

[63] Continuation-in-part of Ser. No. 534,051, Sep. 26, 1995, Pat. No. 5,681,742.

[51] Int. Cl.⁶ .................................................. A61B 17/43
[52] U.S. Cl. ................................ 600/33; 600/34; 600/35; 435/307.1
[58] Field of Search .............................. 435/307.1, 308.1, 435/809; 600/33–35; 604/55, 906

[56] References Cited

U.S. PATENT DOCUMENTS 5,288,415   2/1994   Chen-Wu et al. ..................... 210/781

*Primary Examiner*—John P. Lacyk
*Assistant Examiner*—Rosliand Kearney
*Attorney, Agent, or Firm*—Don Halgren

[57] ABSTRACT

The present invention includes a closed sterile in-vitro fertilization system to provide incubation for an oocyte. The system comprises a pouch having a flexible front and a flexible back wall joined at their outer peripheries. The pouch is divided into a first and a second segregated chamber. An entry port is arranged in each of the chambers through the wall of the pouch. A vacuum means is arranged in the first chamber, to permit direct aspiration of an oocyte from an ovary into that chamber, and an entry conduit is arranged between the first and the second chambers, to permit an oocyte to be transferred therebetween.

10 Claims, 4 Drawing Sheets

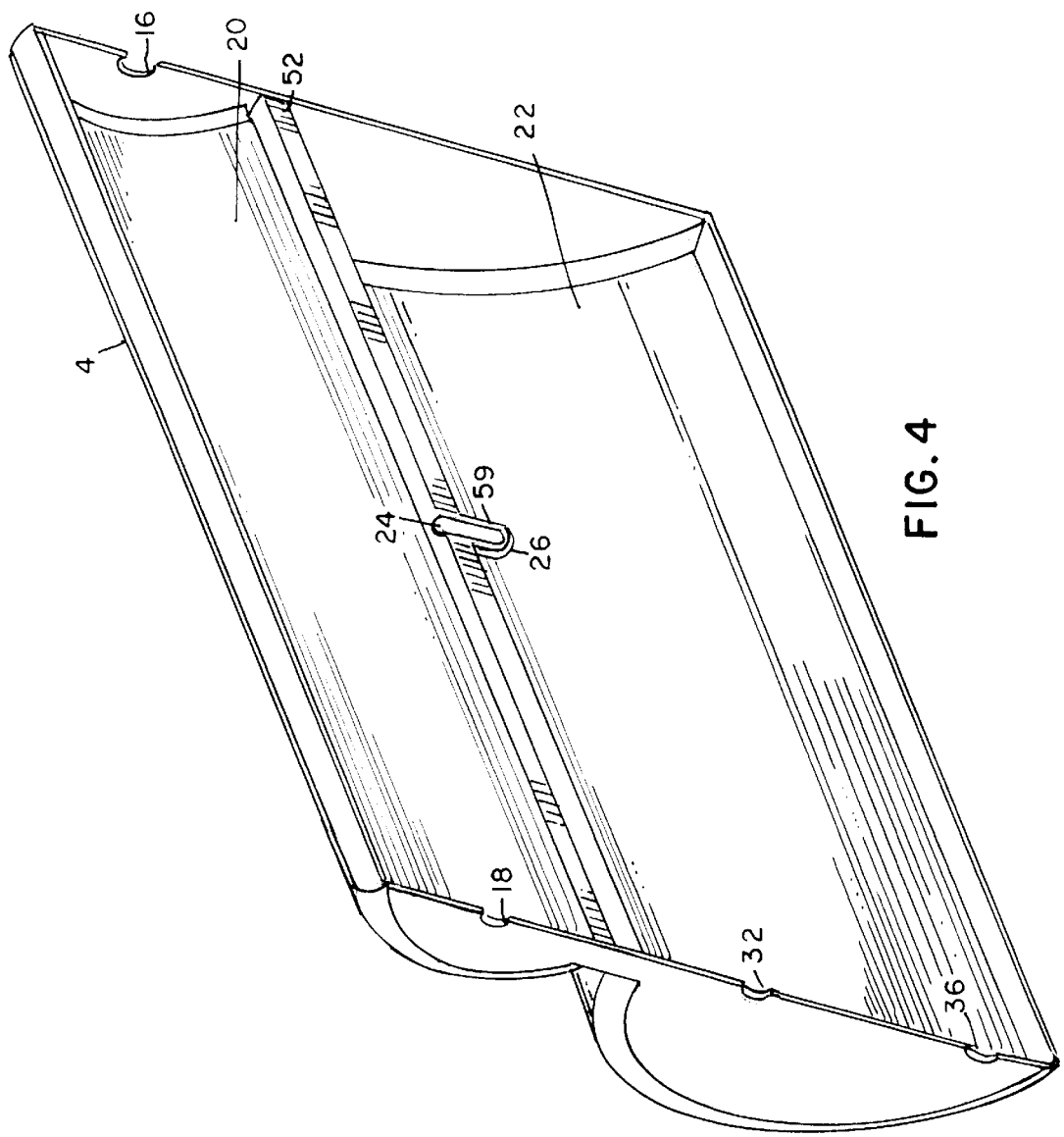

BIOLOGICAL SPECIMAN CONTAINMENT AND INCUBATION POUCH

This application is a continuation-in-part application of our earlier filed, U.S. patent application Ser. No. 08/534,051, filed Sep. 26, 1995, now U.S. Pat. No. 5,681,742, which is incorporated herein by reference, in its entirety.

BACKGROUND OF THE INVENTION

1. Field of the invention

This invention relates to biological specimen containment devices, and more particularly to a chamber useful for in vitro fertilization cultures.

2. Prior Art

Containment devices for biological specimens often are restricted in their design function. The devices often must not permit light to strike the medium within the container. The device must not have sharp edges which would bind or unintentionally agitate the medium within the container. The device must also often permit the medium to be maintained at a desired precise temperature, and the device must often minimize the exposure of the medium to the atmosphere.

One such containment device is shown in U.S. Pat. No. 4,598,045 to Masover et al. issued on 1 Jul. 1986. This patent discloses a container shaped like a cylinder, having a screw on cap. The container however, is designed to permit microscopic examination of the medium without opening of the container.

A further biological specimen containment device is shown in U.S. Pat. No. 4,761,379 to Williams et al. This device however, utilizes a wide-natured opening, which could expose many biological specimens to the atmosphere for too long a period of time, and as such, would not be useful for procedures involving specimens for example, in vitro fertilization processes because of potential atmospheric contamination.

A further biological container is described in U.S. Pat. No. 5,135,865 to Ranoux, wherein a thin walled tube having a rounded lower end and a screw-on cap on its upper end, for containment and fertilization of human ovocytes with minimal $CO_2$ exposure to the medium.

It is an object of the present invention to provide a biological specimen container which overcomes the disadvantages of the prior art.

It is a further object of the present invention to provide a flexible biological pouch-like container which readily permits examination of the contents of the container, from the outside thereof.

It is yet a further object of the present invention, to provide a biological specimen container which permits biological samples to be taken and directly transferred without outside contamination.

BRIEF SUMMARY OF THE INVENTION

The present invention relates to a biological specimen containment device specifically for intravaginal placement of fertilized ovocytes. The containment device is a flexible, thin membrane pouch having at least two specialized segregated containment enclosures therewithin. At least one frangible seal separates the segregated containment portions.

In a first preferred embodiment of the present invention, a flexible resilient containment pouch is made from a thin film of polymer material of the dimensions of about three centimeters by three centimeters square and about one half centimeter thick at its middle.

The pouch has a left side and a right side, the pouch also having a first chamber and a second chamber. The left side of the pouch has a connection which is arranged for the receipt of a Luer fitting. The Luer fitting on the left side of the pouch is arranged to receive an aspiration syringe. The Luer fitting connection permits access into the first chamber of the pouch. The first chamber of the pouch is otherwise known as an aspiration chamber. The left side of the pouch also has a Luer fitting connection for receipt of a second Luer fitting. The second chamber is an incubation chamber. The incubation chamber is in communication with a lowermost Luer fitting connection so as to receive a spermatozoa Luer fitting so as to permit spermatozoa to be introduced through the Luer fitting and into the incubation chamber. Each introduction port may be removed from the respective Luer fittings on the aspiration chamber and on the incubation chamber, and leave them sealed once the Luer fittings themselves have been removed therefrom.

An aspiration syringe is utilized to retrieve an egg from an ovary. The aspiration syringe includes an actuatable plunger, a sealing base, and an aspiration needle. The aspiration needle is in communication with and extends from the right hand side of the aspiration chamber. The aspiration chamber is removable from the incubation chamber, by a frangible seal therebetween.

An oocyte collection chamber is arranged within the incubation chamber, at the juncture of the frangible seal between the aspiration chamber and the incubation chamber. The oocyte collection chamber provides a volume in which an egg will be deposited subsequent to its suctioned entry into the aspiration chamber.

The aspiration chamber has a pair of pull tabs extending radially outwardly from each side thereof. Each pull tab permits the flexible walls of the aspiration chamber of the pouch to be pulled outwardly so as to expand and cause a suction upon the aspiration needle to ensure the introduction of the egg into the (follicle) aspiration chamber. The incubation chamber comprises the volume in which the culture media, spermatozoa, and the unfertilized egg will incubate.

The oocyte collection chamber has a frangible seal thereon which may be broken, so as to permit the introduction of the egg into the incubation chamber, surrounding the oocyte collection chamber.

Culture media is to be introduced into the pouch through the upper Luer fitting on the incubation chamber by means of a syringe or other type of transferring device. The oocyte aspiration needle will aspirate an egg from a ovarian follicle. This aspiration is a suction action so as to create a vacuum in the aspiration chamber facilitated by pulling outwardly on the finger tabs on the side walls of that chamber. The aspiration may also be accomplished by utilizing the syringe connected to the lure fitting attached to the aspiration chamber, by withdrawing the plunger from the barrel of the housing, thus assisting in the creation of the vacuum within that aspiration chamber.

After the egg has been introduced within the aspiration chamber, it is allowed to settle into the smaller oocyte collection chamber. The frangible seal on the oocyte collection chamber may be readily fractured, so as to permit the introduction of the unfertilized egg and a small volume of aspirated fluid into the lower incubation chamber within the lower portion of the pouch. The upper or aspiration chamber and lower or incubation chamber are then sealed and may be detached from one another at their frangible juncture.

Spermatozoa may be introduced through the lowermost Luer fitting within the incubation chamber, the spermatozoa or lower Luer fitting may then be removed from the incubation chamber which chamber is then self-sealed and awaits further in-vitro placement.

Thus, the present invention provides minimum manipulation of biological specimens to produce an in-vitro fertilization system, than that shown by the prior art. The pouch arrangement permits the aspiration of an egg follicle directly into the containment device. The pouch, manufactured from a soft flexible membrane polymeric material has barrier properties, yet permits gas permeability. The flexibility of such a pouch avoids irritation to vaginal mucosa typical of a hard specimen container as may be found in the prior art. Such a pouch arrangement permits the biological sample to be also continuously protected from environmental exposure, to be fully sterile, and to be continuously sealed. A pH indicator may be attached to the inside of the lower pouch, for visual determination thereof.

The invention thus comprises a closed sterile in-vitro fertilization system to provide incubation for an oocyte including a pouch having a flexible front and a flexible back wall joined at their outer peripheries, a first and a second segregated chamber arranged in the pouch, an entry port in each of the chambers through the wall of the pouch. A vacuum means is arranged in the a first chamber, to permit direct aspiration of an oocyte from an ovary into the chamber. An entry conduit is arranged between the first and the second chambers, to permit an oocyte to be transferred therebetween. An aspiration needle is arranged to extend from the first chamber in the pouch, to permit direct communication with an ovary for withdrawal of an oocyte therefrom. A syringe may be arranged in communication with the first chamber to permit a suction to be applied to the aspiration needle extending from the first chamber. A pair of pull tabs are arranged on the outside walls of the first chamber, to permit the walls to be pulled upon and the second chamber to be flexibly expanded to allow a suction to be applied to the aspiration needle extending from the first chamber. The first and second chambers are separated by a frangible seal extending across the pouch, to permit the chambers to be separated after an oocyte has been transferred into the second chamber. A further chamber is arranged within the second chamber, and is in communication with the first chamber, the further chamber comprising an oocyte collection chamber, the collection chamber having a frangible wall portion to permit an egg to be transferred into the second chamber upon receipt and settling into the collection chamber. The walls of the pouch are transparent, to permit observation and control of an oocyte therewithin. The walls of the pouch are gas permeable.

The invention includes a method of arranging a closed sterile in-vitro fertilization system to provide incubation for an oocyte comprising the steps of: providing a pouch having a flexible front and a flexible back wall joined at their outer peripheries; dividing the pouch into a first and a second segregated chamber; cutting an entry port in each of the chambers through the wall of the pouch; attaching a vacuum means onto the first chamber, to permit direct aspiration of an oocyte from an ovary into that chamber; and placing an entry conduit between the first and the second chambers, to permit an oocyte to be transferred therebetween. The invention also includes a method of performing a closed sterile in-vitro fertilization operation to provide incubation for an oocyte comprising the steps of: aspirating an ovary to withdraw a oocyte therefrom, by an aspiration needle; directing the oocyte into a first chamber of a pouch having a flexible front and a flexible back wall joined at their outer peripheries, and the pouch having a first and a second segregated chamber; and settling the oocyte into an entry conduit between the first and the second chambers, to permit an oocyte to be transferred therebetween.

BRIEF DESCRIPTION OF THE DRAWINGS

The objects and advantages of the present invention will become more apparent, when viewed in conjunction with the following drawings in which:

FIG. 4 is an enlarged view in a perspective arrangement showing one half of the pouch system.

DESCRIPTION OF THE PREFERRED EMBODIMENTS

Figure 1:
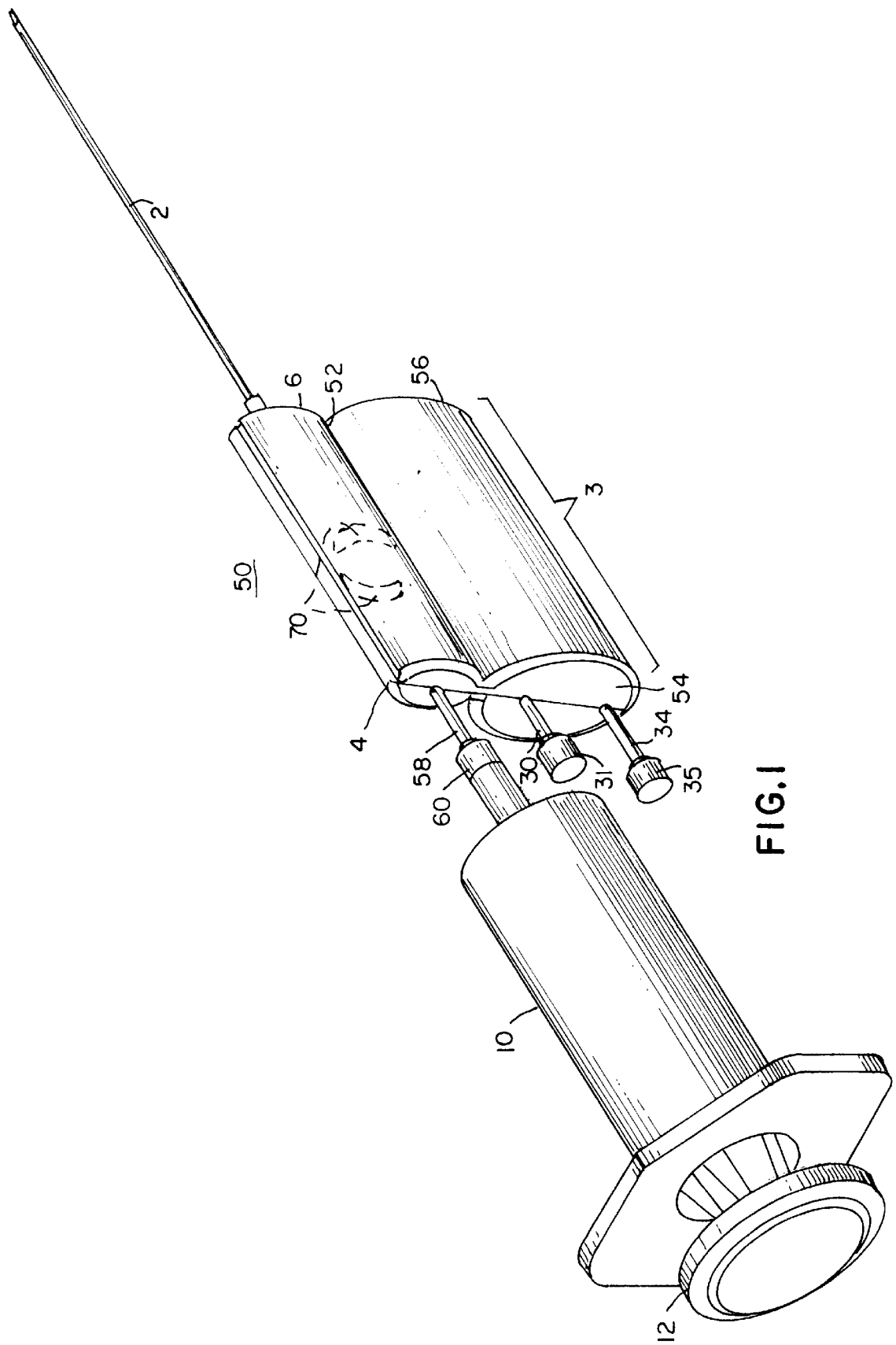
FIG. 1 is a perspective view of a flexible pouch system for in vitro fertilization, showing an aspiration syringe attached therewith.

Referring to the drawings in detail, and particularly to FIG. 1, there is shown the present invention which relates to a biological specimen containment device 50 specifically for intravaginal placement of fertilized oocytes. The containment device 50 is a flexible, thin membrane pouch 3 having at least two specialized segregated containment enclosures 20 and 22 therewithin. At least one frangible seal 52 separates the segregated containment portions.

In a first preferred embodiment of the present invention, a flexible resilient containment pouch 50 is made from a thin film of polymer material of the dimensions of about three centimeters by three centimeters square and about one half centimeter thick at its middle.

The pouch 50 has a left side 54 and a right side 56, the pouch 50 also having the first chamber 20 and a second chamber 22. The left side 54 of the pouch 50 has a connection 58 which is arranged for the receipt of a Luer fitting 60 or like connector arrangement. The Luer fitting 60 on the left side 54 of the pouch 50 is arranged to receive an aspiration syringe 10. The Luer fitting connection 58 permits access into the first chamber 20 of the pouch 50. The first chamber 20 of the pouch is otherwise known as an aspiration chamber. The left side 54 of the pouch 50 also has a Luer fitting connection 30 for receipt of a second Luer fitting 31. The second chamber 22 is an incubation chamber. The incubation chamber 22 is in communication with a lowermost Luer fitting connection 34 so as to receive a spermatozoa Luer fitting 35 so as to permit spermatozoa to be introduced through the Luer fitting connection 34 and into the incubation chamber 22. Each introduction port 58, 30 and 34 may be removed from the respective Luer fittings 60, 31 and 35 on the aspiration chamber 20 and on the incubation chamber 22, and leave them sealed once the Luer fittings themselves have been removed therefrom.

An aspiration syringe needle 2 is utilized to retrieve an egg from an ovary. The aspiration syringe 10 includes an actuatable plunger 12, a sealing base 14, and the aspiration needle 2. The aspiration needle 2 is in communication with and extends from the right hand side 56 of the aspiration chamber 20. The aspiration chamber 20 is removable from the incubation chamber 22, by a frangible seal 52 therebetween.

Figure 2:
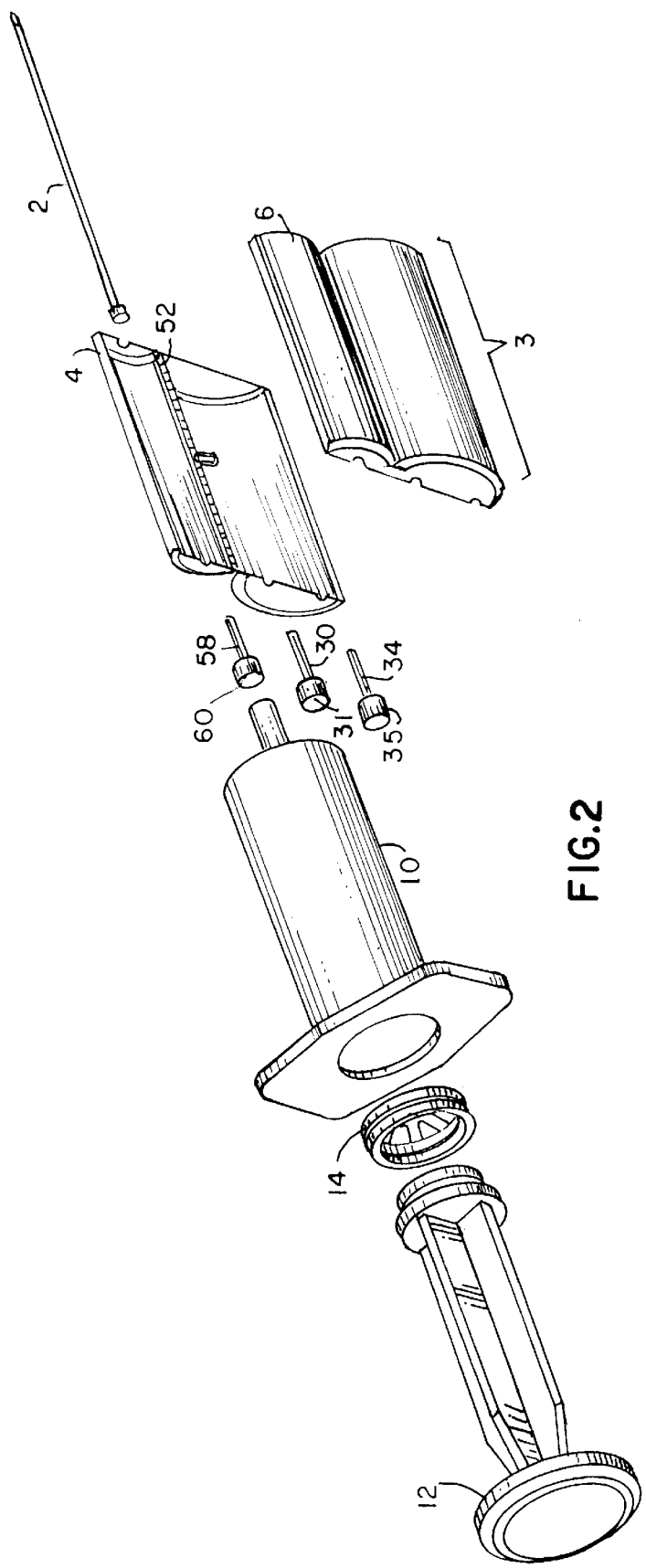
FIG. 2 is an exploded view of the pouch and aspiration syringe shown in FIG. 1.
Figure 3:
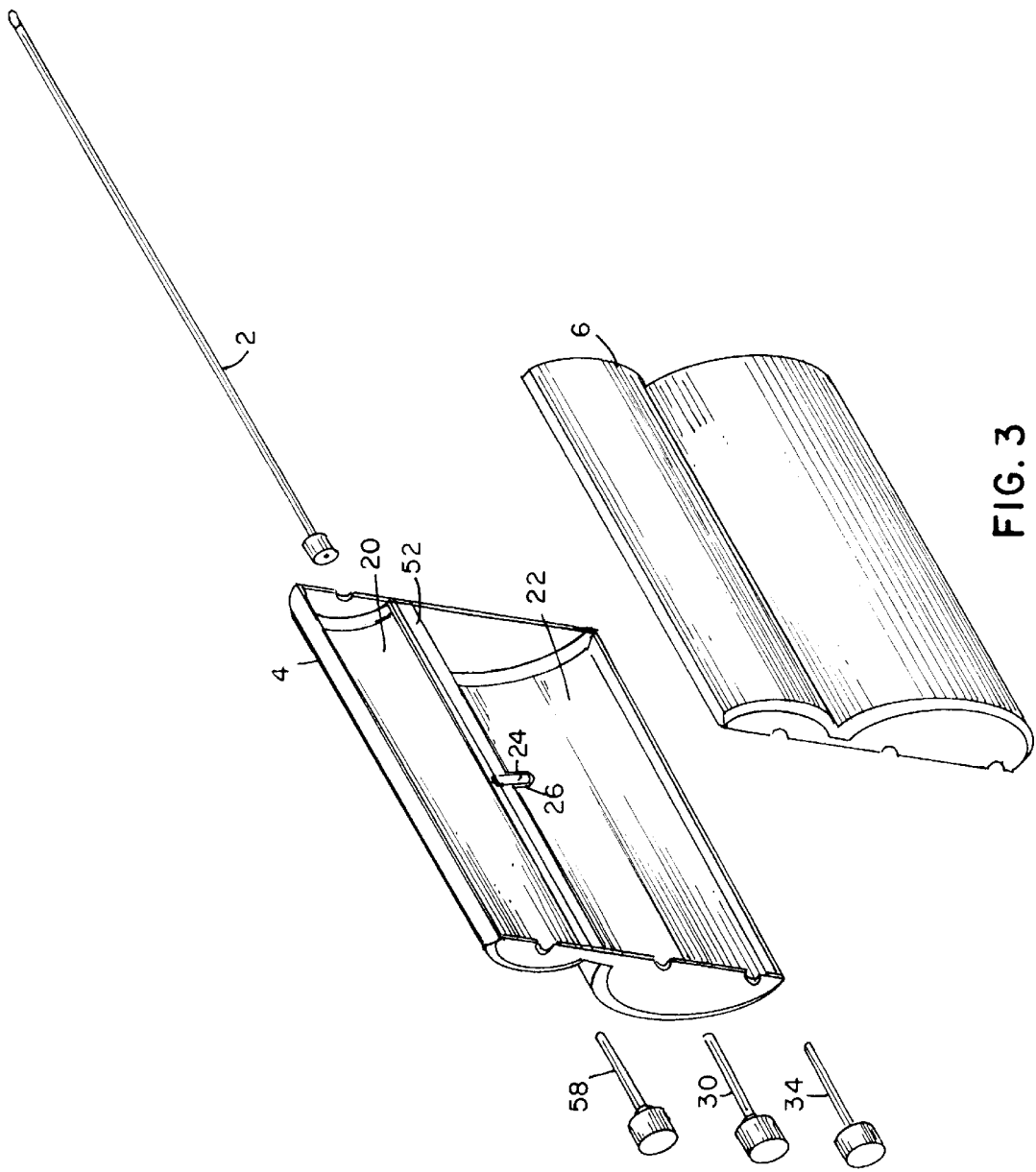
FIG. 3 is an exploded view of the flexible pouch and lure fittings arranged therewith.

An oocyte collection chamber 24 shown in FIGS. 2, 3 and 4, is arranged within the incubation chamber 22, at the juncture of the frangible seal 52 between the aspiration chamber 20 and the incubation chamber 22. The oocyte collection chamber 24 provides a volume in which an egg will be deposited subsequent to its suctioned entry into the aspiration chamber 20.

The aspiration chamber 20 has a pair of pull tabs 70, as shown in FIG. 1, extending radially outwardly from each side thereof. Each pull tab 70 permits the flexible walls of the aspiration chamber 20 of the pouch 50 to be pulled outwardly so as to expand and cause a suction upon the aspiration needle 2 to ensure the introduction of the egg into the (follicle) aspiration chamber 20. The incubation chamber 22 comprises the volume in which the culture media, spermatozoa, and the unfertilized egg will incubate.

The oocyte collection chamber 24 has a frangible seal 59 thereon which may be broken, so as to permit the introduction of the egg into the incubation chamber 22, surrounding the oocyte collection chamber 24.

Culture media is to be introduced into the pouch 50 through the upper Luer fitting 30 on the incubation chamber by means of a further syringe or other type of transferring device, not shown. The oocyte aspiration needle 2 will aspirate an egg from a ovarian follicle. This aspiration is a suction action so as to create a vacuum in the aspiration chamber 20 facilitated by pulling outwardly on the finger tabs 70 on the side walls of that chamber 20. The aspiration may also be accomplished by other suction means such as utilizing the syringe 10 connected to the lure fitting 60 attached to the aspiration chamber 20, by withdrawing the plunger 12 from the barrel of its housing, thus assisting in the creation of the vacuum within that aspiration chamber 20.

After the egg has been introduced within the aspiration chamber 20, it is allowed to settle into the smaller oocyte collection chamber 24. The frangible seal 59 on the oocyte collection chamber 24 may be readily fractured, so as to permit the introduction of the unfertilized egg and a minimal volume of aspirated fluid into the lower incubation chamber 22 within the lower portion of the pouch 50. The upper or aspiration chamber 20 and lower or incubation chamber 22 are then sealed and may be detached from one another at their frangible juncture 52.

Spermatozoa may be introduced through the lowermost Luer fitting 35 within the incubation chamber, the spermatozoa or lower Luer fitting 35 may then be removed from the incubation chamber 22 which chamber 22 is then self-sealed and awaits further in-vitro placement.

Thus, the present invention provides minimum manipulation of biological specimens to produce an in-vitro fertilization system, than that shown by the prior art. The pouch arrangement permits the aspiration of an oocyte directly into the containment device. The pouch, manufactured from a clear, soft flexible membrane polymeric material has barrier properties, yet permits gas permeability. The flexibility of such a pouch avoids irritation to vaginal mucosa typical of a hard specimen container as may be found in the prior art. Such a transparent pouch arrangement permits the biological sample to be also continuously protected from environmental exposure, to be fully sterile, and to be continuously sealed.

We claim:

1. A closed sterile in-vitro fertilization system to provide incubation for an oocyte comprising:

a pouch having a flexible front and a flexible back wall joined at their outer peripheries;

a first and a second segregated chamber arranged in said pouch;

an entry port in each of said chambers through said wall of said pouch;

a vacuum means arranged with respect to said first chamber, to permit direct aspiration of an oocyte from an ovary into said chamber; and an entry conduit between said first and said second chambers, to permit an oocyte to be transferred therebetween.

2. The in-vitro fertilization system as recited in claim 1, including:

an aspiration needle arranged to extend from said first chamber in said pouch, to permit direct communication with an ovary for withdrawal of an oocyte therefrom.

3. The in-vitro fertilization system as recited in claim 2, including:

a syringe arranged in receivable communication with said first chamber to permit a suction to be applied to said aspiration needle extending from said first chamber.

4. The in-vitro fertilization system as recited in claim 2, including:

a pair of pull tabs arranged on said walls of said first chamber, to permit said walls to be pulled upon and said second chamber to be flexibly expanded to allow a suction to be applied to said aspiration needle extending from said first chamber.

5. The in-vitro fertilization system as recited in claim 1, wherein said first and second chambers are separated by a frangible seal extending across said pouch, to permit said chambers to be separated after an oocyte has been transferred into said second chamber.

6. The in-vitro fertilization system as recited in claim 5, wherein a further chamber is arranged within said second chamber, and is in communication with said first chamber, said further chamber comprising an oocyte collection chamber, said collection chamber having a frangible wall portion to permit an egg to be transferred into said second chamber upon receipt and settling into said collection chamber.

7. The in-vitro fertilization system as recited in claim 5, wherein said walls of said pouch are transparent, to permit observation and control of an oocyte therewithin.

8. The in-vitro fertilization system as recited in claim 5, wherein said walls of said pouch are gas permeable.

9. A method of arranging a closed sterile in-vitro fertilization system to provide incubation for an oocyte comprising:

providing a pouch having a flexible front and a flexible back wall joined at their outer peripheries;

dividing said pouch into a first and a second segregated chamber;

cutting an entry port in each of said chambers through said wall of said pouch;

attaching a vacuum means onto said first chamber, to permit direct aspiration of an oocyte from an ovary into said chamber; and placing an entry conduit between said first and said second chambers, to permit an oocyte to be transferred therebetween.

10. A method of performing a closed sterile in-vitro fertilization operation to provide incubation for an oocyte comprising:

aspirating an ovary to withdraw a oocyte therefrom, by an aspiration needle;

directing the oocyte into a first chamber of a pouch having a flexible front and a flexible back wall joined at their outer peripheries, and said pouch having a first and a second segregated chamber; and settling the oocyte into an entry conduit between said first and said second chambers, to permit an oocyte to be transferred therebetween.

* * * * *